United States Patent [19]

Priest

[11] Patent Number: 5,391,723
[45] Date of Patent: Feb. 21, 1995

[54] OLIGONUCLEOTIDE CONJUGATES

[75] Inventor: John H. Priest, Everett, Wash.

[73] Assignee: NeoRx Corporation, Seattle, Wash.

[21] Appl. No.: 18,482

[22] Filed: Feb. 16, 1993

Related U.S. Application Data

[63] Continuation of Ser. No. 825,285, Jan. 22, 1992, abandoned, which is a continuation of Ser. No. 359,783, May 31, 1989, abandoned.

[51] Int. Cl.$^6$ .............................................. C07H 15/12
[52] U.S. Cl. ..................................... 536/23.1; 530/402
[58] Field of Search ........................ 536/23.1; 530/402

[56] References Cited

FOREIGN PATENT DOCUMENTS 0263740 4/1988 European Pat. Off. .
0273085 6/1988 European Pat. Off. .

OTHER PUBLICATIONS

Cheng et al. (1983) Nucl. Acids Res. vol. 11, No. 3, 659–664.
Chu et al. (1983) Nucl. Acids Res. vol. 11, No. 18, pp. 6513–6524.
Caruthers, M. H. Chapter 3, "DNA Synthesis for Nonchemists: The Phosphoramidit Method on Silica Supports", In Synthesis and Applications of DNA and RNA (S. Narang, ed.) Academic Press, New York, pp. 47–94 (1987).
Chu et al., Nucl. Acids Res. 11(18): 6513–6529, 1983.
Cheng et al., Nucl. Acids Res. 11(3): 659–669, 1983.

*Primary Examiner*—Amelia Burgess Yarbrough
*Attorney, Agent, or Firm*—Burns, Doane, Swecker & Mathis

[57] ABSTRACT

There is disclosed an oligonucleotide strand or duplex-targeting protein conjugate, a linking group to link an oligonucleotide to a targeting protein, and a method for producing targeting protein conjugates containing oligonucleotide strands or duplexes. A suitable linker is a bifunctional phosphoramidite ester that binds to both the targeting protein and the oligonucleotide strand or duplex. The invention can be used for delivering chemotherapeutic agents to target sites based upon the specificity of the targeting protein and to deliver specific oligonucleotide sequences to a target site to hybridize and inhibit the expression of complementary sequences within the target cell genome.

14 Claims, 1 Drawing Sheet

OLIGONUCLEOTIDE CONJUGATES

This application is a continuation of prior application Ser. No. 07/825,285, filed Jan. 22, 1992, which is a continuation of application Ser. No. 07/359,783, filed May 31, 1989, both abandoned.

TECHNICAL FIELD

The present invention relates to oligonucleotide-targeting protein conjugates in general, and more particularly, to such conjugates joined through a linking group and optionally having a chemotherapeutic agent associated therewith.

BACKGROUND OF THE INVENTION

Recent efforts have been devoted to the conjugation of cytotoxic agents or neoplastic drugs to specific antibodies, such as monoclonal antibodies, to produce targeting protein conjugates that can selectively kill target cells (e.g., tumor cells) while sparing normal tissues. A large number of different cytotoxic agents (including beta- and alpha-emitting isotopes, plant and bacterial toxins) and a variety of drugs (including antibiotics, antiviral agents, intercalating agents, antimalarial agents, antimetabolites, antineoplastic agents, antifungal agents, and alkylating agents) have been contemplated for this purpose.

Conjugation of chemotherapeutic drugs to antibodies is undertaken for the following reasons:

1. It has recently been shown that up to a 1,000-fold increase in the amount of drug delivered to tumor cells can be attained when the drug is conjugated to an antigen-specific monoclonal antibody over the amount of delivered drug attained by the addition of free drug.
2. Pleiotropic drug resistance may arise following treatment with one of a number of chemotherapeutic drugs, resulting in the inducement of resistance to drugs of several classes. The mechanism(s) of pleiotropic drug resistance are not entirely understood, but it is known that this resistance can be partially overcome by antibody targeting of drugs.
3. Even though current chemotherapeutic drugs are active against only some of the major tumor types, the chemotherapeutic response rate in drug-insensitive tumor types may be increased by antibody-mediated delivery.
4. Many dose limiting toxicities, which are now seen with chemotherapeutic drugs, can be decreased by conjugation to an antibody. A decrease in toxicity with at least equal efficacy would give a superior product, and such a product would have a higher therapeutic index.

Many chemotherapeutic drugs have been conjugated to monoclonal antibodies using a variety of covalent bonds (see, for example, Ghose et al., *Meth. Enzymol.* 93:280 (1983); Ram et al., *Pharm. Res.* 4:181 (1987)). One problem with covalent conjugation of drugs to antibodies is a concomitant loss of drug activity. It is believed that the strength of the covalent bond results in an inability to separate drug from antibody at the target site. Thus, there is a need in the art for a method for binding drugs to targeting agents that permits efficient release of the conjugated drug at the target site.

SUMMARY OF THE INVENTION

The present invention provides targeting protein conjugates wherein an oligonucleotide, as a single-strand or a duplex, is attached to the targeting protein via a linking group as described herein. These conjugates optionally facilitate delivery of a therapeutic agent to a target site.

The present invention also provides, in one aspect, linkers which can covalently bind an oligonucleotide strand or duplex to a targeting protein.

In other words, the oligonucleotide-targeting protein conjugates of this aspect of the present invention are as follows:

Oligonucleotide———Linker—Targeting Protein
(duplex or single strand)

Therapeutic oligonucleotide-targeting protein conjugates of the present invention may be depicted as follows:

Therapeutic———Oligonucleotide———Linker—Targeting
Agent         (duplex or single strand)         Protein or Therapeutic—Linker———Oligonucleotide———Linker—Targeting
Agent             (duplex or single strand)         Protein Each conjugate of the present invention comprises a targeting protein bound (preferably covalently) to a linking group, which in turn is bound (preferably covalently) to an oligonucleotide strand that can be a single strand or a duplex. The oligonucleotide strand can bind a therapeutic agent directly, such as by complementary strand binding of the therapeutic agent. Alternatively, the oligonucleotide strand can bind to a complementary strand to form a duplex that is capable of binding therapeutic agents, such as through intercalation or by major or minor groove binding. Furthermore, the oligonucleotide strand can be bound to a second linking group that, in turn, binds to a therapeutic agent.

In yet another aspect, the present invention provides a DNA oligonucleotide that acts as an oligonucleotide probe, thereby supplementing the targeting capability of the oligonucleotide-targeting protein conjugate. In this aspect of the invention, the oligonucleotide (probe) can improve specificity of therapeutic agent delivery, and/or can serve to intracellularly target the conjugate, subsequent to extracellular delivery to target cells by the targeting protein component of the conjugate. Hybridization of the oligonucleotide (probe) and the target cell DNA will inhibit expression of specific nucleotide sequences within the target cell (by oligonucleotide binding to target cell DNA sequences). This inhibition of DNA translation can be enhanced by the synergistic action of a chemotherapeutic agent whose mechanism of action is inhibition of DNA expression. Synergism is achieved by attaching such chemotherapeutic agent to the oligonucleotide, which can be single- or double-stranded DNA, RNA or analogs thereof.

DETAILED DESCRIPTION OF THE INVENTION

The following are definitions of terms used to describe the invention.

A functional group, as used herein, is that part of a molecule that can interact and form an association or bond with another group. Exemplary of such functional groups are amino groups, hydroxyl groups, carboxy groups and sulfhydryl groups.

Non-covalent bonds are ionic bonds, hydrogen bonds, pi-pi bonds, hydrophobic interactions and van der Waals interactions. A covalent bond is a sigma bond between two atoms.

The oligonucleotide may be covalently or non-covalently bound to the linking group. The therapeutic agent may be covalently or non-covalently bound to the oligonucleotide by several mechanisms. The mechanisms of non-covalent interaction include:

1. Intercalation into a double-stranded oligonucleotide.
2. Non-covalent binding to the major groove or minor groove of a double-stranded oligonucleotide.
3. Hydrogen-bonding to the purine and pyrimidine bases of a single-stranded oligonucleotide.
4. Binding to a single-stranded oligonucleotide by non-covalent interactions between the therapeutic agent and a complementary or partially complementary oligonucleotide.

The present invention encompasses oligonucleotide-protein conjugates having these components:

(1) a single or double stranded oligonucleotide portion;
(2) a protein portion;
(3) a linker capable of linking the oligonucleotide portion and the protein portion, wherein the linker is a nucleotide, nucleotide derivative or a precursor thereof.

As such, the present invention encompasses a class of linker compounds which bind an oligonucleotide strand or duplex of DNA or RNA to targeting protein. Preferably the linker covalently binds to the targeting protein.

Linking groups suitable for use in the present invention are a nucleotide, a nucleotide derivative or a precursor thereof. Exemplary of a linking group contemplated by the present invention is a phosphoramidite compound, such as a phosphoramidite ester. Such an ester is a model for a class of heterobifunctional reagents for linking DNA, RNA, nucleic acids and oligonucleotides to proteins using a variety of combinations of functional groups. Further exemplary of linking groups useful in the practice of the present invention are phosphotriester compounds. Phosphoramidite esters of or ethyl esters of orotic acid or derivatives thereof are also capable of serving as a linking group in the present invention.

Preferably, the linking group is a phosphoramidite ester of an omega-hydroxy carboxylic acid. In one embodiment, the linking group is a phosphoramidite ester having the formula:

wherein $R_1$ is an organic moiety consisting of a bridging portion not capable of substantial interaction with the protein portion and a functional group capable of covalently binding to the protein portion under conditions sufficient to preserve the biological activity of the protein;

$R_2$ is selected from cyanoethyl or $C_{1-10}$—OH; and $R_3$ and $R_4$, taken singly, are selected from alkyl, aryl, aralkyl, cycloalkyl, cycloalkyl-alkyl moieties containing 1 to 10 carbon atoms;

$R_3$ and $R_4$, taken together, constitute an alkylene chain forming a saturated heterocyclic moiety of up to 5 ring carbon atoms with the nitrogen atom to which they are attached, said alkylene chain being optionally substituted with alkyl groups; or $R_3$ and $R_4$, taken together, form a saturated heterocyclic moiety with the nitrogen atom to which they are attached, said heterocyclic moiety containing at least one additional heteroatom selected from the group consisting of nitrogen, oxygen and sulfur. The $R_3$, $R_4$ and N portion of the linker is the site of oligonucleotide binding. $R_1$ is the site of targeting protein binding.

More specifically, the organic moiety $R_1$ contains a functional group suitable for protein binding. Exemplary of such functional groups are ester groups, thiol groups, disulfide groups, or amine groups. The functional group may contain a leaving group, such as —H, $(CH_2)n$—$CH_3$, wherein n is an integer from 1–50. When the functional group is a thiol group or an amino group, a protecting group is preferably bonded thereto. Examples of suitable protecting groups include acetyl for thiol functional groups and trifluoroacetyl for amino functional groups.

When the functional group of $R_1$ is a carboxyl group it may also be protected by a protecting group. Exemplary protecting groups are alkyl, cyclohexyl, cyclopentyl, cyclobutyl, $C_6H_5$, $C_{10}H_7$, other aromatic alcohols, $(-C_2H_4O)_9R$, tetrahydrofuranyl, tetrahydronaphthyl, decahydronaphthyl, $(-CH_2-CF_{2n+1})$ perfluoroalkyl where n is an integer between 1 and 10, methyleneperfluoroalkyl and other alcohols.

The functional portion of $R_1$ is connected to the oxygen atom of the phosphoramidite group of the linker through a nonreactive organic bridge. This connecting portion of $R_1$ is from about 1 to about 40 atoms in length, wherein the atoms are selected from the group consisting of carbon, oxygen, nitrogen, sulfur, phosphorus, hydrogen, and combinations thereof. Exemplary connecting portions are —$(CH_2)_m$—$C_6H_3$—, -cis-$(CH_2)_m$—C=CH—, —$(CH_2)_m$—O—tetrahydrophenyl-, —$(CH_2)_m$—O—ortho-phenyl-, and isomers thereof, R—S—R, R—SO—R, R—SO$_2$R, R—CONH—R, R—S—S—R, R—OCO—R, R—NHCO—R, -continued and other alkyls with relatively nonreactive functional groups, wherein m is an integer from 0 to 20 and j is an integer from 1 to 10; and wherein R is $(CH_2)_k$, wherein k is an integer from 1 to 50, and isomers of the alkyl moiety including isopropyl, t-butyl, as well as cyclo-$C_6H_{10}$, cyclo-$C_5H_8$, cyclo-$C_4H_6$, cyclo-$C_3H_4$, $(CH_2)_m C_6H_4$ where m is defined as above, $C_6H_4(CH_2)_m$ where m is defined as above, tetrahydronaphthyl, $C_{10}H_{10}$, decahydronaphthyl, $C_{10}H_{16}$, $C_6H_5$, aromatic alcohols, halo-substituted alkyl, tetrahydrofuranyl, heterocyclic rings with low reactivity, and other alkyl groups with relatively nonreactive functional groups.

Preferably, substituent $R_1$ contains a series of atoms separating the functional group from the phosphoramidite group. This separation may be accomplished by at least one inert atom, such as the carbon atom in a methylene group, —$CH_2$—.

Any reactive groups present in the bridging portion of the linkers of the present invention should be different from the functional group available for reaction with the protein portion of the conjugate. That is, any reactive moieties within the bridging portion of $R_1$ should react with proteins under different reaction conditions than the functional group on the functional portion of the substituent, if at all.

Preferably, $R_2$ is beta-cyanoethyl and $R_3$ and $R_4$ are each isopropyl. Most preferably, the linker is an O-beta-cyanoethyl N,N-diisopropyl phosphoramidite ester of methyl-omega-hydroxy caproate.

A general preparatory method to form phosphoramidite conjugates of the present invention involves coupling the linker compound to an oligonucleotide sequence attached to a solid resin in a DNA synthesizer (such as one that is commercially available from Applied Biosystems). In this preparatory approach, a free hydroxyl group at the 5' end of the single stranded oligonucleotide sequence displaces the N,N-diisopropylamine of the phosphoramidite ester to form a phosphotriester. The standard coupling cycle is modified to accommodate the fact that the trityl protecting group may not be used with some linkers, and other conditions of the coupling cycle may be altered by one skilled in the art to accommodate the particular chemistry of the linker.

Usually deprotection of protected functional groups, both on the linker and on the oligonucleotide, can be accomplished simultaneously with resin removal if the conditions are chosen by one skilled in the art. For example, if the functional group on the linker is a carboxyl group protected as a methyl ester then the standard ammonia treatment for deprotection and resin removal should not be used since the carboxyl groups will from amides. Instead, brief treatment with hydroxide will simultaneously accomplish deprotection, ester hydrolysis and resin removal.

However, some protected functional groups have to be deprotected in a separate step which can be accomplished either before or after resin removal. If it is accomplished before resin removal, both the agents used for deprotection and the protecting groups can be washed off of the resin and, thus, will not contaminate the final oligonucleotide complex preparation. If deprotection is accomplished after resin removal, then the oligonucleotide complex may have to be purified. This can readily be accomplished using a variety of chromatographic or other methods chosen by one skilled in the art including ion exchange, gel permeation, affinity chromatography or ethanol precipitation.

A more specific example of this methodology involves coupling a linker containing a carbomethoxy group to a resin-bound oligonucleotide sequence in a DNA synthesizer. After simultaneous deprotection (should the oligonucleotide contain any protecting groups), ester hydrolysis and resin removal, the newly formed carboxylic acid is activated with a carbodiimide such as 1-ethyl-3-(dimethylaminopropylcarbodiimide) (EDAC). N-hydroxysuccinimide, N-hydroxybenzotriazole, or tetrafluorophenol is added to form an active ester in situ. This activated carboxyl group can then be reacted with a targeting protein or peptide to form a covalent oligonucleotide-linking group-protein or -peptide conjugate.

In addition, the oligonucleotide can be hybridized with its complementary sequence, if desired, to form a double-stranded oligonucleotide duplex as part of the protein conjugate. The hybridization reaction can occur either before or after conjugation with the targeting protein.

In other words, the conjugates of this aspect of the present invention are as follows:

Another aspect of the present invention involves a therapeutic oligonucleotide-protein conjugate comprising:

(1) a single or double stranded oligonucleotide portion;
(2) a therapeutic agent capable of chemically associating with said oligonucleotide portion;
(3) a protein portion; and
(4) a linker capable of linking said oligonucleotide portion and said protein portion, wherein said linker is a nucleotide, nucleotide derivative or a precursor thereof.

Therapeutic conjugates of this aspect of the present invention may be depicted as follows:

or

The first conjugate depicted above is an example of direct conjugation or association of the therapeutic agent and the oligonucleotide. Bond A represents a covalent or a non-covalent interaction. The second conjugate is representative of indirect conjugation of the therapeutic agent and oligonucleotide via a second linker moiety capable of linking the oligonucleotide portion and therapeutic agent.

The targeting protein/linking group/oligonucleotide (double- or single-stranded) conjugates of the present invention can deliver specific DNA or RNA sequences to the target site. The therapeutic agent conjugates of the present invention can deliver either or both the therapeutic agent and specific DNA or RNA sequences to the target site. Such deliveries are accomplished via binding of the targeting protein (e.g., antibody or antibody fragment) to its receptor molecule at the target cell (e.g., antigenic determinant). The conjugate, or a portion of it, can be internalized into a target cell by a number of mechanisms. The mechanisms of cellular uptake include receptor-mediated endocytosis (involving coated pits for some antibody-based conjugates), pinocytosis, or nonreceptor-mediated endocytosis. If the targeting protein is not an antibody or antibody fragment, but an endogenous growth factor, such as growth factor type alpha (alpha-TGF) or, for example, a cloned segment of Pseudomonas exotoxin A, the targeting protein itself can effectuate translocation into the target cell.

Once the conjugate of the present invention is internalized within the cell, the ability of the oligonucleotide and/or therapeutic agent to release from the conjugate can be affected by the presence of pH-sensitive bonds in the structure of the linker of the conjugate. In a preferred embodiment, the bonds of the linker can hydrolyze under the mildly acidic conditions of the cellular endosome. The hydrolyzable bonds within the linker include ester linkages and certain amide linkages. Moreover, an intercalated therapeutic agent is generally acid sensitive; therefore, release within an endosome may be facilitated. Also, it should be noted that bonds such as disulfide bonds are acid reducible and, as a result, are also pH sensitive.

In the therapeutic agent-containing conjugate of the present invention, the use of a conjugate comprising a targeting protein, therapeutic agent and a single- or double-stranded DNA-, RNA-, or DNA-RNA hybrid oligonucleotide allows for target-specific delivery of a therapeutic agent. The therapeutic agent is non-covalently or covalently bound to the oligonucleotide moiety of the conjugate, however the therapeutic agent is not so tightly bound to the conjugate that decreased dissociation of the therapeutic agent risks reduced potency thereof. The targeting protein directs the conjugate to the target site.

In forming therapeutic conjugates, the selective deprotection and activation of functional groups of the linker and/or oligonucleotide permits the formation of an oligonucleotide-linker conjugate. After deprotection or activation of a second functional group on the linker, a targeting protein, such as an antibody or antibody fragment, is added to form a covalently bound oligonucleotide-linker-antibody or antibody fragment conjugate. A therapeutic agent may then be added under reaction conditions sufficient to achieve association or conjugation of that agent with the oligonucleotide portion of the conjugate.

As an oligonucleotide useful in the conjugates of the present invention, there is contemplated single- or double-stranded DNA, RNA or a DNA-RNA hybrid. These oligonucleotides can be produced by conventional oligonucleotide synthesizers. Moreover, the oligonucleotides of the present invention can be formed, in whole or in part, from non-natural nucleotide bases.

Many non-natural nucleotide bases are known to those having skill in the oligonucleotide production art and include, for example, alkylated (e.g., $Cl_{1-6}$ alkyl) natural bases (preferably methylated), phosphorothioate and phosphonate oligonucleotides. The use of non-natural nucleotide bases alters the charge density and, thus, the membrane permeability of the oligonucleotide or the groove structural characteristics of the oligonucleotide, especially in the major groove, thereby altering the affinity of a drug for an oligonucleotide duplex.

In one embodiment of the conjugate aspects of the present invention, the conjugate is used to facilitate the delivery of oligonucleotide sequences complementary to a segment of a nucleic acid sequence or sequences within the genome of the target cell. The result is an inhibition of the expression of this portion of the target cell genome. An exemplary use of such conjugates involves target tumor cells and the specific genome sequence confers the rapid growth or metastatic characteristics of the tumor cell, such as an oncogene. Another such use involves virus-infected target cells, wherein the viral genome serves as the target oligonucleotide sequence.

The oligonucleotide conjugate may be targeted to the target cell by an antibody or antibody fragment, while the oligonucleotide portion of the conjugate is complementary to a tumor oncogene, viral genome or a portion thereof. Further, the oligonucleotide-targeting protein conjugate may also contain a chemotherapeutic agent whose cytotoxic mechanism of action is inhibition of transcription or translation. Such chemotherapeutic inhibition of protein synthesis will further aid in the inhibition of tumor cell genome expression.

The protein portion of the conjugate of the present invention is a protein capable of targeting the conjugate to target tissue. Such a targeting protein may be a protein, polypeptide, or fragment thereof that is capable of binding to a desired target site in vivo. The targeting protein of the present invention may bind to a receptor, substrate, antigenic determinant, or other binding site on a target cell or other target site.

A targeting protein may be modified (e.g., to produce variants and fragments of the protein), as long as the desired biological property (i.e., the ability to bind to the target site) is retained. A targeting protein may be modified by using various genetic engineering or protein engineering techniques. Typically, a protein will be modified to more efficiently bind to the target cell binding site.

Examples of targeting proteins include, but are not limited to, antibodies and antibody fragments; serum proteins; fibrinolytic enzymes; peptide hormones; and biologic response modifiers. Among the suitable biologic response modifiers which may be used are lymphokines, such as interleukin (e.g., IL-1, -2, -3, -4, -5, and -6) or interferon (e.g., alpha, beta and gamma), erythropoietin, and colony stimulating factors (e.g., G-CSF, GM-CSF, and M-CSF). Peptide hormones include melanocyte stimulating hormone, follicle stimulating hormone, luteinizing hormone, and human growth hormone. Fibrinolytic enzymes include tissue-type plasminogen activator, streptokinase and urokinase. Serum proteins include human serum albumin and the lipoproteins.

Antibodies useful as targeting proteins may be polyclonal or monoclonal, with monoclonal antibodies (MAbs) specific for target cell recognition being preferred. A number of monoclonal antibodies that bind to a specific type of cell have been developed. These include MAbs specific for tumor-associated antigens in humans. Exemplary of the many MAbs that may be used are anti-TAC, or other interleukin-2 receptor antibodies; NR-ML-05, or other antibodies that bind to the 250 kilodalton human melanoma-associated proteoglycan; NR-LU-10, a pancarcinoma antibody directed to a 37–40 kilodalton pancarcinoma glycoprotein; and OVB3, which recognizes an as yet unidentified, tumor-associated antigen. Antibodies derived through genetic engineering or protein engineering may be used as well.

The antibody employed as a targeting agent in the present invention may be an intact molecule, a fragment thereof, or a functional equivalent thereof. Examples of antibody fragments useful in the conjugates of the present invention are F(ab')$_2$, Fab' Fab and Fv fragments, which may be produced by conventional methods or by genetic or protein engineering.

In some embodiments, the oligonucleotide portion of the present invention may serve as an additional or auxiliary targeting portion. The oligonucleotide portion may be selected or designed to assist in extracellular targeting, or to act as an intracellular targeting moiety. That is, the oligonucleotide portion may act as a DNA probe seeking out target cells. This additional targeting capability will serve to improve specificity in delivery of the conjugate to target cells. The oligonucleotide may additionally or alternatively be selected or designed to target the conjugate within target cells, while the targeting protein targets the conjugate extracellularly.

Therapeutic agents useful in the conjugates of the present invention may be traditional chemotherapeutic drugs, such as adriamycin or another anthracycline derivative, or drugs having a mechanism of action that damages or cleaves the complementary DNA sequence (see, for example, the iron-EDTA complex described by Dervan (*Science* 232:464, 1986), which cleaves complementary DNA sequences). Other DNA cleaving agents, such as iron porphyrins, as well as other agents that react with DNA to inactivate it, such as 2,4-diaziridinyl benzophenone and melphelan are also suitable for use within the invention.

Many chemotherapeutic drugs of different classes bind to DNA. DNA binding is a particularly common trait of antiviral agents and antineoplastic agents. The mechanisms of chemotherapeutic agent binding to DNA include intercalation of duplex or double-stranded DNA; binding to the major or minor groove of duplex DNA in a double helix; complexation with double-stranded DNA, RNA or DNA-RNA hybrids; and covalent or non-covalent general interactions with either single or double-stranded DNA or RNA by a variety of mechanisms.

One class of chemotherapeutic agents, the intercalating agents, binds to double-stranded DNA. The intercalation process involves several non-covalent interactions within an oligonucleotide duplex. The generally accepted requirements for successful intercalation have been deduced from "direct techniques" that measure three fundamental features of the configuration of the DNA helix: (a) the DNA helix must be extended; (b) the DNA helix must be locally unwound; and (c) the plane of the aromatic chromophore of the bound intercalating drug must be parallel to that of the DNA base pairs (ostensibly more or less perpendicular to the helix axis). The required DNA helical extension has been verified by autoradiographic and electron microscopic measurements of the contour length of DNA molecules in the presence of intercalating drugs.

The most readily applicable technique for determining the presence or extent of drug intercalation into DNA is simply to measure the enhancement of viscosity of sonicated rod-like DNA fragments. Local unwinding is evidenced by monitoring the effects of drug binding on the superhelical state of circular DNA. As the level of intercalative drug binding rises, the negatively (right-handed) supercooled state of a naturally occurring circular DNA is progressively diminished, lost, and reversed in a characteristic fashion that can be observed by following the sedimentation coefficient, the viscosity, or the mobility in gels.

Stable complexes of drug moiety and single- or double-stranded DNA have been formed upon in vitro or in vivo delivery of intercalating-type cytotoxic drugs to DNA. A targeting protein (such as antibody) attached to DNA may serve as a targeting carrier for an intercalating drug. However, DNA, in duplex form, has not been conjugated to an antibody. This optimal use has never been achieved, since it is difficult to efficiently attach an oligonucleotide or double-stranded DNA or RNA to an antibody or an antibody fragment.

From the foregoing, it can be seen that drugs which can be intercalated within DNA are also useful in the present invention. Such drugs include ethidium, proflavine, daunomycin, adriamycin, actinomycin, ellipticine, tilorone, m-AMSA, mithramycin, netropsin, irehdiamine A, anthramycin, steptonigrin, bleomycin, ditercalinium, triostin, echinomycin, other bis-intercalating agents, and derivatives thereof.

One class of intercalating agents, the anthracyclines, includes antibiotics having a mode of action that depends on intercalative binding to DNA. Daunomycin and adriamycin are the best known representatives of the anthracycline class, which also includes nogalamycin, cinerubin, rhodomycins and rubomycins. All are characterized by a tetrahydrotetracenaquinone chromophore that contains three flat, coplanar, six- membered rings. The phenoxazone chromophore of actinomycin is in essential respects comparable in size and shape to other intercalating agents.

These antibiotics are identified as intercalating agents, and reasonably detailed molecular models for their binding to DNA have been formulated. The daunomycin-DNA model places the aromatic portion of the chromophore between successive DNA base pairs in fairly classical intercalative fashion, while the puckered fourth cyclohexene ring with its attached daunosamine (amino sugar) substituent projects into the groove of the helix. Additional stabilization comes from strong electrostatic interaction between the charged amino group and nearby DNA phosphate residues, as well as from some hydrogen bonding interactions.

Actinomycin requires deoxyguanosine-containing nucleotides to properly bind DNA. The phenoxazone chromophore intercalates more or less symmetrically between two GC base pairs, with hydrogen bonds connecting the two amino groups of the guanine bases to the carbonyl groups of the threonine residues in the peptide lactone rings, which pack neatly into the narrow groove of the DNA helix. This results in tight binding of the actinomycin to only a single GC base pair.

Ellipticine is another example of an intercalating drug. Its helix-unwinding angle is indistinguishable from that of the simple aminoacridines. Ellipticine's mode of intercalative binding has been confirmed by the structure of a crystalline intercalative complex with a dinucleotide.

Tilorone intercalates with double-stranded DNA characterized by a low unwinding angle. Tilorone has a strong preference for AT-rich regions of duplex DNA.

Related classes of chemotherapeutic agents are the bis-intercalators. Examples of bis-intercalators include naturally occurring triostin, echinomycin and derivatives such as TANDEM (a tetranormethyl derivative of triostin). An advantage of the bis-intercalators is their ability to bind to a double-stranded oligonucleotide through numerous non-covalent interactions, thereby increasing binding affinity. Increased binding affinity lowers the amount of circulating free chemotherapeutic agent, reducing toxicity associated with the chemotherapeutic agent. However, since the ultimate site of chemotherapeutic action of a bis-intercalator is target cell or viral DNA, the bis-intercalator will bind approximately equally as well to target DNA as it does to the carrier conjugate.

Another class of chemotherapeutic agents generally binds to the major or minor groove of double-stranded or duplex DNA. Examples of chemotherapeutic agents in this class include netropsin and berenil. Many of the agents bind to defined nucleotide sequences, which permits these preferential sequences of nucleotide to be used as preferred carriers of these chemotherapeutic agents.

Cellular DNA is the primary target of many chemotherapeutic agents, including antineoplastic agents and antiviral drugs. Many alkylating agents bind noncovalently to DNA before alkylation. Examples of alkylating agents are melphelan, dicarbazine and thioTEPA. An oligonucleotide conjugate can provide an effective delivery vehicle for an alkylating agent, as compared to administration of free drug, by reducing the toxic side effects associated with administration of the free alkylating agent. Many alkylating agents are bifunctional or multi-functional, and can produce cross-links between DNA strands.

Cis-platinum non-covalently binds to pyrimidine nucleotides. The non-covalent binding of cis-platinum yields a strong bond that leads to DNA-DNA and DNA-protein crosslinking. Therefore, a pyrimidine-containing oligonucleotide-targeting protein conjugate associated with cisplatinum will have significant therapeutic advantages.

Yet another class of chemotherapeutic agents that can be delivered by an oligonucleotide conjugate include polyamines, spermine and spermidine analogs, and poly-L-lysine.

Radionuclides are also useful as therapeutic or diagnostic agents. Exemplary radionuclides include diagnostic imaging agents, such as Tc-99m, I-123, Cu-67, Ga-67, Ga-68, Zr-89, In-111, I-131, Ru-97, Pb-203, Sn-177 m and combinations thereof; and therapeutic radionuclides, such as Rh-105, I-125, Re-188, An-199, At-211, Pb-212 and combinations thereof.

The therapeutic agent is noncovalently or covalently bound to the oligonucleotide portion of the conjugate. If the therapeutic agent is covalently bound to the oligonucleotide, the therapeutic agent may be bound to a naturally occurring or synthetic nucleoside base (e.g., 5-iodo-uracil, 5-bromo-uracil, 5-fluoro-uracil, 6-mercaptopurine, mercaptoguanine, thiouracil, uracil mustard derivative, a base-radionuclide derivative, such as 5-I-125-uracil, 5(p-I-131)- or 5(p-At-211-benzamidyl)uracil, or an orotic acid amide of an amine-containing drug, such as daunomycin or melphelan); or the therapeutic agent may be linked to the end of the oligonucleotide strand opposite the linking group/targeting protein portion.

The therapeutic agent may be covalently linked to the same oligonucleotide strand to which the targeting protein is bound, when the oligonucleotide is a single strand or a duplex, or the therapeutic agent may be linked to the complementary oligonucleotide strand, when the oligonucleotide is a duplex. Selection of the length of the complementary strand allows for control of the binding affinity of the non-covalently bound therapeutic agent. The therapeutic agent may also intercalate within double-stranded DNA and be carried by the conjugate within the two strands of DNA.

Many methods exist for attaching functional groups to the 5' end of synthetic oligonucleotides (see, for example, Haralambidis et al., *Nucl. Acids Res.* 15:4857, 1987). Exemplary methods for attaching functional groups to the 3' end of synthetic oligonucleotides are described by Zuckerman et al., Nucl. Acids Res. 15:5305, 1987.

The attached functional group(s) of the inventive linker can be derivatized with one or more heterobifunctional linkers. A heterobifunctional linker, as defined herein, links two different groups having different chemical reactivities. For instance, a heterobifunctional linker can react with one functional group on the inventive linker and provide a different reactive group for reaction with therapeutic agent or targeting protein. The latter functional group can be either native to the therapeutic agent or targeting protein or can be provided via the use of a second heterobifunctional agent. A portion of a conjugate of the present invention having the aforementioned "three linker" arrangement may be depicted as follows:

Many heterobifunctional reagents are known, (see, for example, "Bifunctional Reagents" Meth. Enzymol. 91, 580, Academic Press, 1983; Inman, "Affinity Chromatography and Related Techniques", pages 217–233, Elsevier, 1982; Ji, Biochim. Biophys. Acta 559:39–69, 1979; Ji et al., Anal. Biochem. 121:286–89, 1982; and Ishikawa, *Immunoassay* 4:209, 1983). Exemplary heterobifunctional reagents include N-succinimidyloxy bromoacetate, which reacts first with an amine group and then with a thiol group; p-fluorosulfonylbenzoyl chloride, which reacts first with an alcohol or an aromatic or aliphatic amine, and then specifically with a tyrosine hydroxyl; cyanuric chloride, which reacts with a poor nucleophile, such as a hydroxyl or an aromatic amine first, and then with a stronger nucleophile, such as an aliphatic amine in the second reaction; and aziridine, which reacts with a weak nucleophile, such as an aromatic amine or a thiol on a purine or pyrimidine, and yields an aliphatic amine functional group.

There are many appropriate methods for synthesizing conjugates of the present invention that have different molecules on either end of the oligonucleotide. One method uses the same linker at both ends of the oligonucleotide (thus giving two identical functional groups)

and a judicious choice of reaction conditions, known to one of skill in the art to effect the attachment of only one portion of the conjugate to one end of the linking group. A purification step may be needed to separate the desired mono-derivative from the reactants, the di-derivatized oligonucleotide and other products. The second portion of the conjugate can then be attached to the second functional group.

A second conjugation method is analogous to a procedure called "orthogonal synthesis." As applied to the present invention, this method takes advantage of the relative reactivity, under specified reaction conditions, of available (unprotected and unbound) functional groups. A functional group will react with and bind to its complementary functional group only under favorable reaction conditions. Thus, the binding of a functional group to one or another complementary functional group will depend upon the chemical reactivities of the functional groups and the reaction conditions. Therefore, the use of different reaction conditions and different functional groups can determine if and when a linking group will bind. If two linking groups have different functional groups, binding is controlled by the chemical reactivities of the functional groups and the reaction conditions. The same principle applies to heterobifunctional linkers, in that the binding of different functional groups can be controlled by their chemical reactivities and the reaction conditions.

Exemplary of this methodology is the synthesis of a therapeutic agent/linker A/oligonucleotide/linker B/ targeting peptide complex. The two linkers, A and B, can have the same functional groups or different functional groups for binding to the oligonucleotide. After the formation of the linker A/oligonucleotide/linker B portion, sequential reactions to form the final conjugate are undertaken. The reaction binding the therapeutic agent to linker A will involve a different functional group and reaction conditions than the reaction binding linker B to the targeting peptide. Changes in reaction conditions will facilitate sequential binding of the available functional group of linker A to the therapeutic agent, followed by binding of the available functional group of linker B to the targeting peptide (or binding in the opposite order, i.e., linker B, then linker A).

Additional examples of orthogonal synthesis of complex conjugates involve linker A/oligonucleotide/linker B intermediates, in which the first linker (A) has an available thiol functional group, and the second linker (B) has an available amine functional group. First, the reaction conditions are chosen such that the thiol functional group is conjugated to a maleimide or haloacetyl group on a therapeutic agent. The amine functional group can then be conjugated to a carboxyl group on a targeting protein using a water soluble carbodiimide under appropriate reaction conditions.

Alternatively, the second step could feature derivatization of the amine with a maleimide- or haloacetyl-containing heterobifunctional agent, such as N-succinimidyloxy-4(N-maleimido-methyl)-cyclohexane-1 carboxylate (SMCC) or iodoacetic anhydride, and then conjugated to a thiol group on a targeting protein. Alternatively, the second step could feature reaction of the amine functional group with succinic anhydride, with the resultant free carboxylic acid group coupled to an amine group on the targeting protein using carbodiimide.

Moreover, the amine functional group can be reacted with a thiol-containing heterobifunctional reagent, such as iminothiolane or succinimidyloxy-3-2 (2-pyridyldithio)propionate (SPDP), followed by a treatment with a reducing agent, such as $\beta$-mercaptoethanol ($\beta$-ME) or dithiothreitol (DTT). The resultant free thiol group is reacted with a maleimide or haloacetyl derivative of a targeting protein. This derivatization of the targeting protein can be accomplished via reaction with SMCC, iodoacetic anhydride or N-succinimidyloxy-(4-iodoacetyl) aminobenzoate (SIAB) under neutral or slightly alkaline conditions. A disulfide-bonded conjugate can be made using the SPDP-oligonucleotide derivative (unreduced) together with a thiol-containing targeting protein. If the targeting protein does not contain native thiols, a thiol-containing targeting protein is obtained by derivatization with iminothiolane or SPDP, followed by reduction with DTT or $\beta$-ME, or via DTT-mediated reduction of native disulfides.

Another "orthogonal synthesis-type" alternative uses a thiol- or amine-containing linker together with a carboxylic acid-containing linker. The thiol-containing linker can be reacted as described above; the amine-containing linker can be bound to a therapeutic agent or targeting protein by one of the methods described above, selected according to whether the therapeutic agent or targeting protein contains an amino group, maleimide or haloacetyl group, a carboxylic acid, or a thiol group. The carboxylic acid linker is then coupled to amino groups on the targeting protein or drug using carbodiimide. Alternatively, the carboxylic acid linker is converted to a hydrazide by esterification with methanol and addition of hydrazine, and then reacted with an aldehyde to form a stable hydrazone. Aldehydes can be generated on a targeting protein (e.g., an antibody) by periodate oxidation of carbohydrate residues, or by coupling a heterobifunctional linker having an aldehyde functional group to the antibody.

Yet another synthetic procedure involves attachment of a protecting group to the functional group(s) of one of the linkers bound to an oligonucleotide. A first compound (therapeutic agent or targeting protein) is conjugated to the second linker bound to the oligonucleotide. The protecting group is then removed, and the oligonucleotide/first compound conjugate is joined to a second compound (therapeutic agent or targeting protein) via the second, now un-protected, linker. Examples of protecting agents include a disulfide of a thiol functional group, used either as a dimer of the thiol or as a "thiol-like" 2-pyridyl thione or 3-carboxy-4-nitrothiophenol; an S-acetyl group, also for thiols; and 2,3 dimethyl maleic anhydride for amine groups. Other protecting groups are described in "Protective Groups in Organic Synthesis," (TW Greene) John Wiley & Sons, New York, 1981.

A targeting protein will generally contain more than one copy of a complementary functional group that can bind to linker under proper reaction conditions. Thus, if both available linking groups of a "two-linker/oligonucleotide" intermediate have the same functional group and this complex is conjugated to a targeting protein, intramolecular and intermolecular crosslinking will occur. Such crosslinking results in non-desired products such as a therapeutic agent bound directly to the targeting protein via only a linker. Also, while it is often possible to purify the therapeutic agent/linker A/oligonucleotide/linker B conjugate from reactants and side products, purification is less easily achieved when targeting protein is conjugated to the "two-linker/oligonucleotide" intermediate.

If the two available functional groups on the two linkers of the linker/oligonucleotide intermediate are different and the complex is conjugated first to a targeting protein and then to a therapeutic agent, it is also possible that the therapeutic agent will couple directly to the targeting protein, instead of to the oligonucleotide. Moreover, many derivatization conditions that are used to couple therapeutic agents to oligonucleotides are considered too harsh to use in the presence of targeting protein. Harsh derivatization conditions can result in a loss of targeting protein biological activity. The same principle applies to conditions for the removal of blocking agents. To avoid these difficulties, the oligonucleotide can be conjugated first to the therapeutic agent, and then to the targeting protein, by selective, serial removal of different blocking agents. However, a variety of conjugation reactions can be performed, and some blocking agents can be removed under relatively mild reaction conditions that do not affect the biological activity of the targeting protein portion.

The following examples are offered by way of illustration, and not by way of limitation.

EXAMPLE 1

Synthesis of a Phosphine Linking Group

Methyl-6-hydroxyhexanoate was made as follows. To a solution of 25 g (220 mmole) of $\epsilon$-caprolactone in 250 ml of methanol was added 12.3 g (220 mmole) of sodium methoxide. The resulting solution was stirred at 25° C. for 12 hours, and then evaporated to dryness. The residue was partitioned between saturated aqueous ammonium chloride and dichloromethane, and the organic layer was washed with saturated aqueous sodium bicarbonate. Drying over magnesium sulfate and removal of the solvent in vacuo yielded methyl-6-hydroxyhexanoate as a clear, colorless oil (21 g; 65% unoptimized).

To a solution of 0.786 g (5.37 mmole) of methyl-6-hydroxyhexanoate and 0.48 g (2.8 mmole) of diisopropylammonium tetrazolide in 25 ml of dichloromethane were added dropwise 1.62 g (5.37 mmole) of bis(-diisopropyl amino)-2-cyanoethyoxyphosphine (Aldrich). The resulting solution was stirred at 25° C. for 2 hours and extracted with phosphate buffer at pH 7. Drying over magnesium sulfate and fast chromatography on silica gel (40% ethylacetate-hexanes, trace triethylamine) yielded the diisopropylamino-5-(carbomethoxy)pentyloxy-2-cyanoethoxy phosphine linking group as a colorless oil (1.30 g: 70%).

EXAMPLE 2

Synthesis of a Monoclonal Antibody-DNA Probe Conjugate

Figure 1:
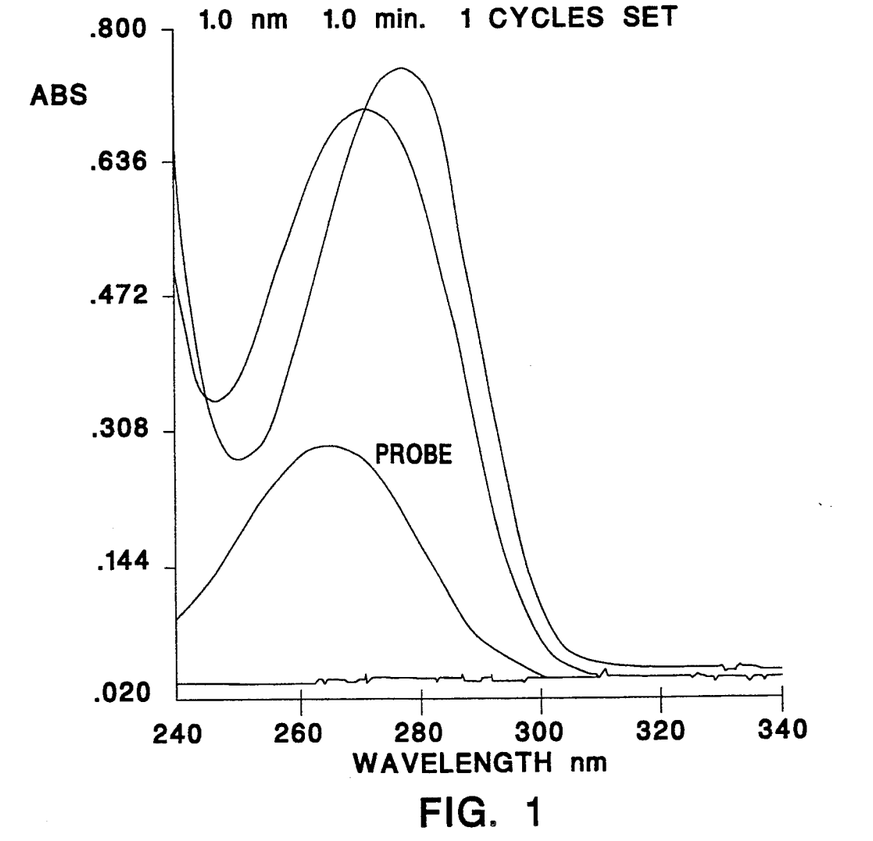
FIG. 1 is an isoelectric focusing (IEF) electrophoresis gel showing IEF markers in column 1, 9.2.27 monoclonal antibody in column 2, a conjugate of 9.2.27 MAb-linker-oligonucleotide in column 3, and a conjugate as in column 3, but additionally bound to the drug adriamycin.

For conjugation to a monoclonal antibody (MAb), to the 5'-phosphodiester of dodecathymine ($T_{12}$) and omega hydroxycaproic acid ($C_5$—COOH), dubbed $T_{12}$-$C_5$—COOH (i.e., DNA probe), in approximately 20 μl water was added 16.8 micromoles of 1-ethyl-3-(dimethylamino propylcarbodiimide) (hydrochloride) in 5.5 μl of water. After 10 minutes at room temperature, 18.6 micromoles of N-hydroxysuccinimide (NHS) was added in 8.7 μl over a course of 70 minutes. To this was added 0.96 mg (6 nmoles) of MAb 9.2.27, which reacts with an antigen present on melanoma cells, in 90 μl of 67 mM carbonate buffer, pH 9.6, followed by an additional 80 μl of 0.2M carbonate buffer for pH adjustment to 9.5. The reaction mix was incubated for 2 hours at 4° C., applied to a 0.8×13 cm Sephacryl S-200 (Pharmacia Fine Chemicals, Piscataway, N.J.) column pre-equilibrated with 6.7 mM phosphate buffer, pH 7.3, in 0.15M NaCl (PBS), and eluted with PBS. Ultraviolet spectra of the eluate reveal that the native antibody had an absorbance maximum at 277 nm and the $T_{12}$-$C_5$—COOH had an absorbance maximum at 265 nm. However, the spectrum of the antibody-DNA probe conjugate showed a 5 nm shift to 272 nm as a result of covalent linkage of the DNA probe (FIG. 1). From the absorbance of the conjugate at two wavelengths, 260 and 290 nm, the concentrations of MAb and oligonucleotide probe can be calculated, and a probe/MAb ratio of 1.6 was obtained.

Figure 2:
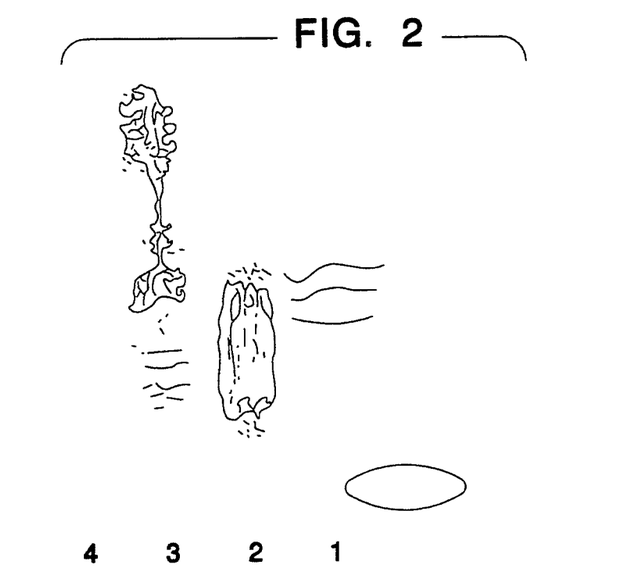
FIG. 2 shows the ultraviolet absorbance spectral shift of native 9.2.27 antibody as compared to a covalently bound oligonucleotide-9.2.27 MAb conjugate.

This conjugate was also analyzed by isoelectric focusing (IEF) gel electrophoresis. In this procedure, a pH gradient was established in an agarose gel in an electric field. When a protein was applied to the gel, it migrates until it reaches the region of the gel where the pH was equal to the isoelectric point of the protein. At this pH, the negative charges on the protein exactly balanced the positive charges, thus it was electrically neutral, and, as such, will not migrate in an electric field. While each monoclonal antibody was a homogeneous protein that had a single amino acid sequence, a monoclonal antibody did not focus on an IEF gel into a single band, but rather displayed a closely spaced family of bands. This microheterogeneity was due to differences in the post-translational glycosylation of the antibody, specifically to differences in the number of sialic acid residues. Thus, the family of bands represented proteins differing from each other by an integral number of charge units. Since the $T_{12}$-$C_5$—COOH probe contained thirteen negative charges, a large shift towards the anode in an IEF gel would be expected with the DNA probe-MAb conjugate. The IEF gel of the conjugate (FIG. 2) indicated the expected large shift towards the anode. Using other derivatives of the MAb as standards, a shift of approximately 25 charge units, or approximately 2 probes/antibody, was found, which is in agreement with the results from UV spectroscopy.

EXAMPLE 3

Synthesis of an Oligonucleotide-Linking Group-Monoclonal Antibody Conjugate

In this example, the tetrafluorophenyl (TFP) ester of $T_{12}$-$C_5$—COOH was synthesized and purified before reaction with MAb. Briefly, to a solution of 0.25 micromoles of $T_{12}$-$C_5$—COOH in 0.310 μl of PBS (phosphate-buffered saline) were added 10 micrograms of TFP in 20 μl of acetonitrile: water (9:1) and 12.5 micrograms of EDAC in 25 μl of water, and the solution was incubated at 75° C. for 20 minutes. After purification on a reverse phase C-18 silica column, 1 ml of 30% acetonitrile/water eluate was evaporated to about 20 μl. To this was added 0.67 mg MAb in 40 μl PBS, 0.46 ml phosphate buffer, pH 9.5, and 40 μl acetonitrile. After 2 hours incubation at 37° C., the conjugate was purified on a Sephacryl S-200 column as in Example 1. Spectral analysis indicated an average of 2.2 oligonucleotides per MAb.

EXAMPLE 4

Formation of an Intercalating Drug/Double-Stranded DNA/Monoclonal Antibody Conjugate A duplex oligonucleotide-MAb complex may be formed in several ways. One method involves hybridization of an oligonucleotide-linker intermediate with its complementary oligonucleotide, and then conjugation of the double-stranded intermediate to targeting protein. A more specialized example involves synthesis of a self-complementary, oligonucleotide-linker derivative, which has the effect of providing two linking groups per duplex DNA. This oligonucleotide-linker derivative is used to improve yields of the conjugation reaction, or to provide another functional group for linking a therapeutic agent to the conjugate.

This example describes the hybridization of oligonucleotide-linker-MAb conjugates (described above) with a complementary oligonucleotide. A special example of this methodology involves derivatization of the complementary oligonucleotide with a drug or a linker that reacts with a therapeutic agent to form a therapeutic agent-(linker)-duplex DNA-linker-MAb conjugate.

To the conjugate synthesized in Example 3 was added 50 nmoles of dodecaadenosine phosphate ($A_{12}$) in 0.5 ml PBS containing 5 mM EDTA, and the hybridization mixture was incubated at 37° C. for 44 hours.

To this reaction mix at room temperature was added 60 μg (30 μl) adriamycin (Adr). After 2 hours at room temperature, the mixture was dialyzed against 50 mM sodium phosphate, 1M NaCl, pH 5.5, for 72 hours, concentrated on a centrifugal ultrafilter ("Centricon") with a 30 Kdalton molecular weight cutoff, and washed three times with 3 ml of the same buffer on the ultrafilter.

Spectral analysis revealed that this conjugate contains 7 molecules of Adr per MAb.

EXAMPLE 5

Synthesis of an Oligonucleotide-Monoclonal Antibody Conjugate Using a Thioether Bond A $T_{12}$-$C_2$—$NH_2$ oligonucleotide derivative was synthesized on an Applied Biosystems DNA synthesizer using standard methods (B-cyano-ethyl phosphoramidite ester of thymidine and "Aminolink-1" [Applied Biosystems, Foster City, Calif.]).

To about 50 nmoles (34 μl) $T_{12}$-$C_2$—$NH_2$ were added 2.4 μmoles (80 μl) N-succinimidyloxy-4(N-maleimidomethyl)cyclohexane-1-carboxylate (SMCC) in dimethylsulfoxide (DMSO) and 25 μl 1M carbonate buffer, pH 9.5. After incubation for 1 hour at room temperature, the reaction mix was applied to a 9.5 ml Sephadex G-25 column (PD-10, Pharmacia, Piscataway, N.J.) and eluted with PBS. A control reaction mix contained underivatized $T_{12}$ (Pharmacia) and SMCC. Simultaneously, a monoclonal antibody, NR-ML-05 (reactive with an antigen on melanoma cells), was incubated with 50 mM dithiothreitol to produce thiol groups from native antibody disulfides. The reduced antibody was purified on a PD-10 column at 0°-4° C., the two fractions containing antibody (by absorbance at 280 nm) were pooled, and 1.5 mg (0.33 ml) aliquots were added to the 1.0 ml fractions containing the $T_{12}$-$C_2$NHCO-SMCC, $T_{12}$, or the same fraction from the SMCC control.

These reaction mixes were incubated for 25 hours at room temperature and then separated on a Superose 12 (Pharmacia, Piscataway, N.J.) gel permeation column. The antibody fraction contained an average of 0.32 $T_{12}$ probes per MAb as compared to the control, which contained none.

From the foregoing, it will be appreciated that, although specific embodiments of the invention have been described herein for purposes of illustration, various modifications may be made without deviating from the spirit and scope of the invention.

What is claimed is:

1. An oligonucleotide-protein conjugate comprising:
   (1) a single or double stranded oligonucleotide portion;
   (2) a protein portion; and
   (3) a phosphoramidite ester linker which links said oligonucleotide portion and said protein portion disposed between the oligonucleotide portion and the protein portion, wherein the linker covalently binds to the protein portion and to the oligonucleotide portion, wherein the linker is of the formula:

and wherein $R_1$ is an organic moiety consisting of a bridging portion not which consists of an active ester which substantial interaction with said protein portion and a functional group capable of covalently binds to said protein portion under conditions sufficient to preserve the biological activity of said protein;

$R_2$ is selected from cyanoethyl or $C_{1-10}$—OH; and $R_3$ and $R_4$, taken singly, are selected from alkyl, aryl, aralkyl, cycloalkyl, cycloalkyl-alkyl moieties containing 1-10 carbon atoms;

$R_3$ and $R_4$, taken together, constitute an alkylene chain forming a saturated heterocyclic moiety of up to 5 ring carbon atoms with the nitrogen atom to which they are attached, said alkylene chain being optionally substituted with alkyl groups; or $R_3$ and $R_4$, taken together, form a saturated heterocyclic moiety with the nitrogen atom to which they are attached, said heterocyclic moiety containing at least one additional heterocyclic heteroatom selected from the group consisting of nitrogen, oxygen and sulfur, wherein the oligonucleotide and protein conjugate components are ultimately linked by a phosphite tri-ester moiety.

2. A conjugate of claim 1, wherein said bridging portion of $R_1$ is selected from the group consisting of $(CH_2)_m$—, —$C_6H_3$—, -cis-$(CH_2)_m$—C=CH—, $(CH_2)_m$-o-tetrahydrophenyl-, —$(CH_2)_m$—O—o-phenyl-, and isomers thereof, R—S—R, R—SO—R, R—$SO_2$—R, R—COHN—R, R—S—S—R, R—O-CO—R, R—NHCO—R, $$R-\underset{\underset{O}{\|}}{C}-O-R, \quad R-O-R, \quad R-\underset{}{N}-R, \quad R(CH=CH)_jR,$$

$$R-\underset{\underset{O}{\|}}{\overset{\overset{O}{\|}}{S}}-NH-R, \quad \text{and} \quad R-\underset{\underset{R}{|}}{\overset{\overset{O}{\|}}{P}}-O$$

wherein R is an alkyl group containing from 1 to 50 carbon atoms, cyclo-$C_6H_{10}$, cyclo-$C_5H_8$, cyclo-$C_4H_6$, cyclo-$C_3H_4$, $(CH2)mC6H4$, $C_6H_4(CH_2)_m$, tetrahydronapthyl, $C_{10}H_{10}$, decahydronapthyl, $C_{10}H_{16}$, $C_6H_5$, aromatic alcohols, tetrahydrofuranyl, and heterocyclic rings; and wherein m is an integer from 0 to 20 and j is an integer from 1 to 10.

3. A conjugate of claim 1, wherein $R_2$ is betacyanoethyl.

4. A conjugate of claim 1, wherein $R_3$ and $R_4$ are isopropyl.

5. A conjugate of claim 1, wherein the linker is O-beta-cyanoethyl N,N-diisopropyl phosphoramidite ester of methyl-omega-hydroxy caproate.

6. A conjugate of claim 1, wherein said oligonucleotide is single-stranded.

7. A conjugate of claim 1, wherein said oligonucleotide is double-stranded.

8. A conjugate of claim 1, wherein a segment of said oligonucleotide portion is capable of extracellular targeting.

9. A conjugate of claim 1, further comprising a therapeutic agent which chemically associated with said oligonucleotide portion.

10. A conjugate of claim 9, wherein said therapeutic agent is chemically associated with said oligonucleotide by binding via a second linker.

11. A conjugate of claim 10, wherein said first linker is bound to said protein portion and said oligonucleotide portion through covalent bonding, and said second linker is bound to said therapeutic agent and to said oligonucleotide portion through covalent bonding.

12. A conjugate of claim 9, wherein said therapeutic agent is chemically associated with said oligonucleotide by covalent bonding.

13. A conjugate of claim 9, wherein said therapeutic agent is chemically associated with said oligonucleotide by non-convalent interaction.

14. A conjugate of claim 13, wherein said oligonucleotide is double-stranded and said therapeutic agent is chemically associated by intercalation into said oligonucleotide.

* * * * *